United States Patent
Millot et al.

(10) Patent No.: US 6,411,853 B1
(45) Date of Patent: Jun. 25, 2002

(54) DEVICE FOR THERAPEUTIC TREATMENT OF WOUNDS

(75) Inventors: Philippe Pierre Marie Millot, Orgeux; Michel Lamoise, Bessey-les-Citeaux, both of (FR)

(73) Assignee: Laboratoires d'Hygiene et de Dietetique (L.H.D.), Paris (FR)

( * ) Notice: Subject to any disclaimer, the term of this patent is extended or adjusted under 35 U.S.C. 154(b) by 0 days.

(21) Appl. No.: 09/462,505

(22) PCT Filed: Jul. 23, 1998

(86) PCT No.: PCT/FR98/01632

§ 371 (c)(1),
(2), (4) Date: Jan. 24, 2000

(87) PCT Pub. No.: WO99/04852

PCT Pub. Date: Feb. 4, 1999

(30) Foreign Application Priority Data

Jul. 25, 1997 (FR) .............................. 97 09506

(51) Int. Cl.⁷ .................................. A61N 1/04

(52) U.S. Cl. .............................. 607/50; 607/115; 602/2

(58) Field of Search .............. 607/50, 152, 115, 607/153, 149; 600/372, 393; 602/2, 56

(56) References Cited

U.S. PATENT DOCUMENTS

| | | | | | |
|---|---|---|---|---|---|
| 2,943,627 A | * | 7/1960 | Howell | ..................... | 128/416 |
| 4,817,594 A | * | 4/1989 | Juhasz | ..................... | 128/155 |
| 4,895,154 A | | 1/1990 | Bartelt et al. | ................ | 128/421 |
| 4,982,742 A | | 1/1991 | Claude | ..................... | 128/798 |
| 5,205,297 A | * | 4/1993 | Montecalvo et al. | ....... | 128/798 |
| 5,320,598 A | * | 6/1994 | Haak et al. | .................. | 604/20 |
| 5,395,398 A | | 3/1995 | Rogozinski | .................. | 607/50 |
| 5,445,606 A | * | 8/1995 | Haak et al. | .................. | 604/20 |
| 6,032,077 A | * | 2/2000 | Pomeranz | .................. | 607/101 |
| 6,051,748 A | * | 4/2000 | Auguste et al. | ............... | 602/54 |

FOREIGN PATENT DOCUMENTS

EP 0 367 320 5/1990
EP 0 504 715 9/1992

* cited by examiner

*Primary Examiner*—Kennedy Schaetzle
(74) *Attorney, Agent, or Firm*—Jacobson Holman, PLLC

(57) ABSTRACT

The invention concerns a device comprising a dressing provided with a layer (8) for absorbing the wound exudates and electric supply means (9) to circulate a current in said wound, through the dressing. The invention is characterized in that said layer (8) consists of a dry hydrophile substantially non-conductive layer at the time it is applied on the wound, the subsequent migration of the exudates into the thickness of said layer (8) controlling the activation of said electric supply means (9), concomitantly with the continuation of the process of exudate absorption by said layer (8).

20 Claims, 2 Drawing Sheets

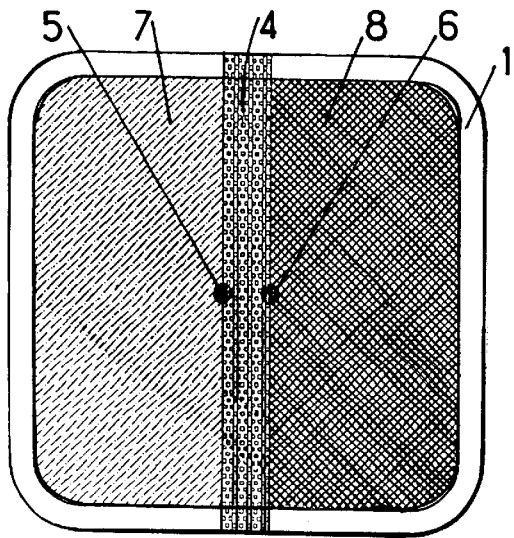
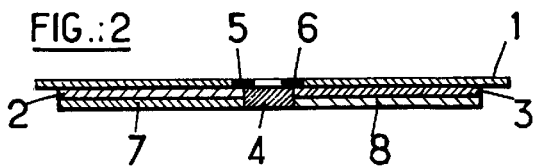
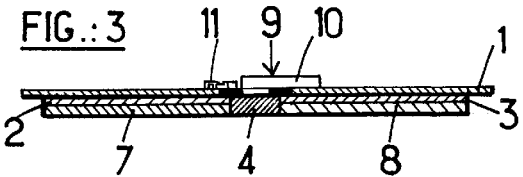
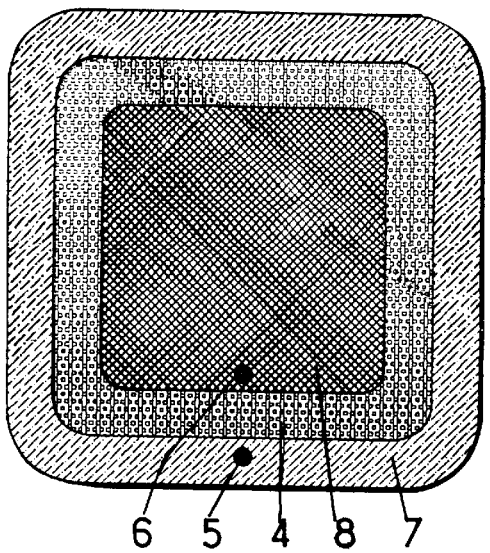
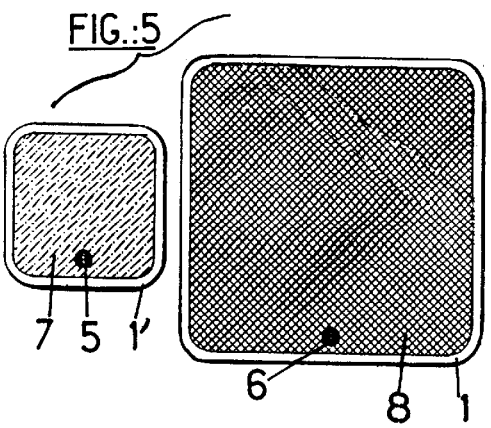
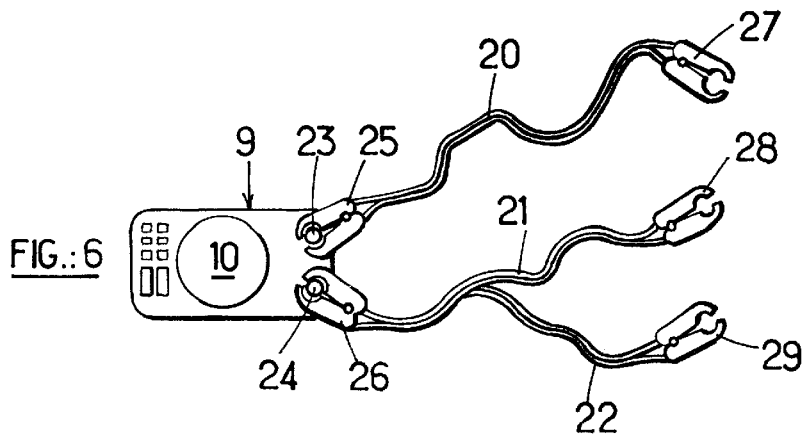

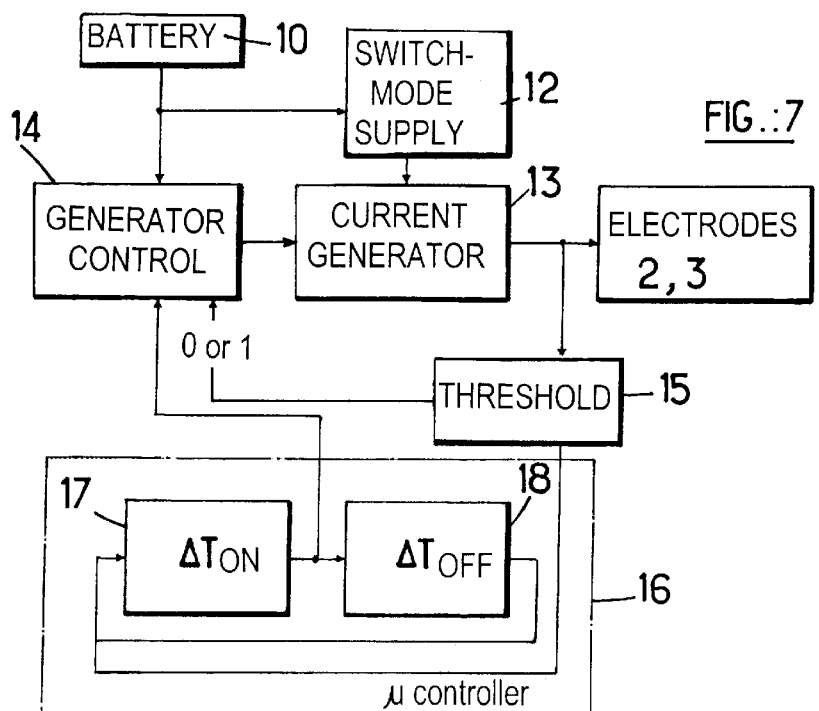
FIG.:7
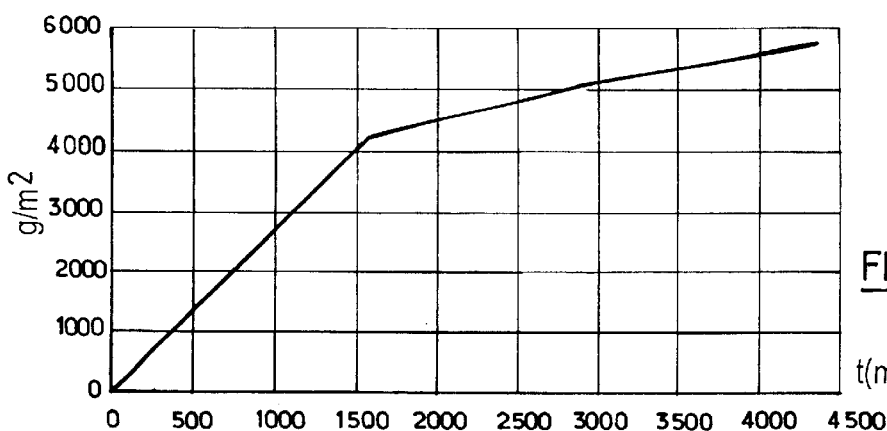
FIG.:8
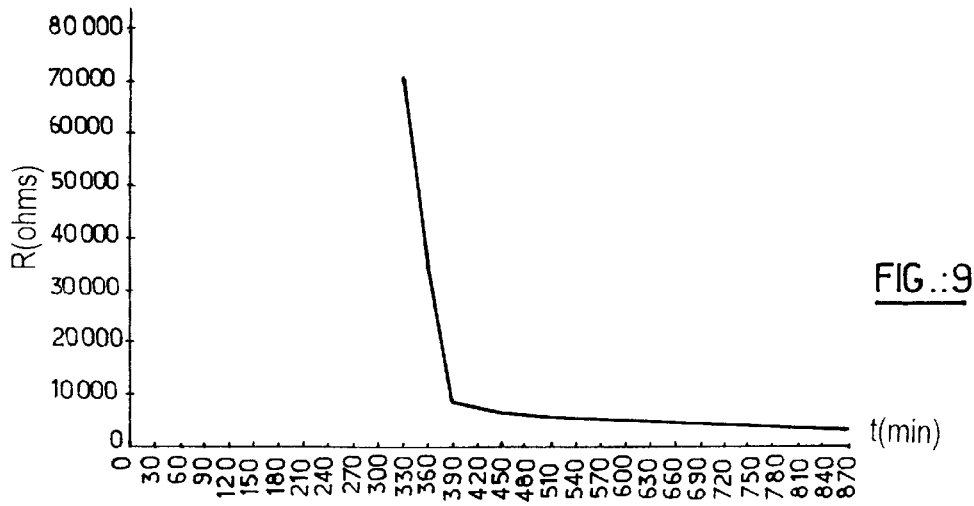
FIG.:9

DEVICE FOR THERAPEUTIC TREATMENT OF WOUNDS

The present invention relates to a device for therapeutic treatment of wounds and, more particularly, to a device of this kind of the type including a dressing provided with a layer for absorbing exudates from the wound and electric supply means to circulate a current in said wound through said dressing.

Many types of dressings have been designed to absorb the exudates from a wound and to accelerate healing of the wound. One such dressing is a semi-occlusive and sterile adhesive dressing consisting of a hydrocolloid mass layer applied to a support consisting of a polyurethane film for local treatment of wounds such as leg ulcers or bed sores. The Chenôve, France company Laboratoires URGO manufactures a dressing of this kind, which is marketed under the ALGOPLAQUE brand (registered trade mark). In contact with a wound, the hydrocolloid particles dispersed in the layer absorb the exudates, swell and form, a moist gel encouraging healing of the wound without the newly formed tissues being damaged when the dressing is renewed.

Electrotherapy of wounds is a known technique for accelerating healing. The technique consists generaly in applying two electrodes to the skin of the patient and passing an electric current between the electrodes so that the current enters a wound in the skin. The document EP-A-0 367 320 describes a wound treatment system including a dressing consisting of an electrically conductive compress, a return electrode and means for passing an electric current between the compress and the return electrode. The compress includes an electrically conductive hydrophile gel layer which can contain up to 93–96% bound water and is rendered conductive by a metallic salt. The gel layer is applied to an electrically conductive layer. An electric current flows in this layer and in the hydrophile gel layer and then in the wound before returning to the return electrode. The capacity of a gel of the above kind to absorb exudates from the wound is limited by its initial moisture content.

The object of the present invention is to provide a device for therapeutic treatment of wounds in which the capacity for absorption of exudates from the wound is maximised, while being combined with an electric treatment of the wound.

This object of the invention, along with others that will become apparent on reading the following description, is achieved with a device for therapeutic treatment of wounds of the type which includes a dressing provided with a layer for absorbing exudates from the wound and electric supply means to circulate a current in said wound, through said dressing, which device is remarkable in that said layer consists of a dry hydrophile layer which is substantially electrically non-conductive at the time it is applied on the wound, subsequent migration of exudates into the thickness of said layer controlling the activation of said electric supply means.

Said initially dry hydrophile layer is therefore used without deterioration of its capacity to absorb exudates. As will be shown later, this initially non-conductive layer becomes conductive as it becomes charged with exudates. It therefore becomes sufficiently conductive at some stage to enable "electric" treatment of the wound.

In this regard, according to one feature of the device in accordance with the present invention, said electric supply means include a circuit for measuring the impedance of the hydrophile layer and means responsive to said measurement falling below a predetermined threshold to command the activation of the electric supply means under nominal conditions.

Other features and advantages of the present invention will become apparent on reading the following description and examining the accompanying drawings, in which:

FIGS. 1 and 2 are respectively a plan view and a sectional view of a first embodiment of a dressing forming part of a device in accordance with the invention and which includes both a "return" conductive electrode and an "active" electrode in contact with the wound, FIG. 3 is a sectional view of a first embodiment of a device in accordance with the invention, consisting of the dressing from FIGS. 1 and 2 and electric supply means integrated into the dressing, FIG. 4 shows a second embodiment of a dressing for a device in accordance with the invention, FIG. 5 shows another embodiment of a dressing for a device in accordance with the invention in which only the "active" electrode is included in the dressing, the "return" electrode being independent thereof, FIG. 6 shows a second embodiment of the electric supply means of a device in accordance with the invention, designed to be associated with the dressing from FIG. 5, FIG. 7 is a functional block diagram of electric supply means of a device in accordance with the invention, and FIGS. 8 and 9 are graphs respectively showing the process of charging with exudates and the evolution of the impedance of a hydrophile layer forming part of a dressing in accordance with the invention.

FIGS. 1 and 2 of the accompanying drawings show that the first embodiment of a dressing forming part of a device in accordance with the invention is substantially flat in shape and rectangular, with a side length of a few centimetres, for example, so as to have a surface area substantially twice that of a wound to be covered.

The dressing includes, on a flexible support 1, two electrodes 2 and 3 separated by a strip 4 of insulative material. The electrodes 2 and 3 are in electric contact with respective electrically conductive material studs 5, 6 which pass through the support 1 and are flush with its outside surface.

One of the electrodes, for example the electrode 2, referred to as the return electrode, is covered with a conductive layer 7 constituting an interface with the skin of the patient. The other electrode 3, referred to as the active electrode, and which is in contact with the wound, is covered, in accordance with the invention, with a dry hydrophile layer 8 which is not electrically conductive in the dry state.

Electric supply means, described in more detail hereinafter with reference to FIG. 7, are connected to the studs 5, 6 to establish and control an electric current flowing between the two electrodes when the dressing is applied to the skin of a patient, the dry hydrophile layer 8 being pressed against a wound to be healed and the conductive layer 7 being applied to an area of the skin adjacent the wound.

For fixing the dressing in this position, adhesive means (not shown) can be provided on the dressing, for example on the support 1, at the periphery thereof.

The electric supply means can be physically separate from the dressing and connected to the studs 5, 6 by electric wires. They can also be integrated into the dressing and discarded with it. FIG. 3 shows such means 9 including an autonomous electric energy source such as a battery 10 and diverse discrete or integrated electronic components 11. The means 9 are fixed to the flexible support 1 above the studs 5, 6. As an alternative to this, these means can be received removably on the dressing, thanks to mechanical assembly means such as press-studs, grooves, meshes, "Velcro"

(registered trademark), etc so that they can be removed after treatment and re-used on a new dressing.

As soon as the dressing is fixed over the wound, the dry hydrophile layer 8 begins to be charged with exudates from the wound. In vitro tests have been carried out to study this process, using cells filled with physiological serum and closed by a sample of a layer 8 consisting of a 1 mm thick hydrocolloid mass in contact with the serum, the latter simulating the exudates from a wound. The kinetics of charging of the physiological serum layer were established by measuring cumulatively the quantity of serum absorbed by the layer between two consecutive measurements. The FIG. 8 graph represents the average kinetics of charging of the cells used.

The evolution of the resistance of the layer was measured by establishing an electric current in the cell, through the layer, at regular time intervals, and measuring the resulting voltage, the current density established during the measurements being 0.11 mA/cm$^2$. The FIG. 9 graph shows the evolution in time of the average of the resistances calculated in this way for the cells used. The graph shows that during the first few hours it was not possible to evaluate the conductivity because the layer 8 remained substantially non-conductive in this period.

The sudden appearance of conductivity in the layer 8, as shown in FIG. 9 and occurring after 6 to 8 hours, can be explained by regular progressive migration of the serum, and therefore of the exudates from a wound, which are rich in mineral salts and therefore highly conductive, from the face of the layer 8 which is in contact with the wound to the other face of that layer, which is in contact with the electrode 3. Thus the resistance of the layer 8 remains high for as long as the exudates have not reached the other face. It drops to a much lower value as soon as the exudates reach that other face. The layer 8 is then conductive throughout its thickness and an electric current can be passed through it, in the case of a treatment seeking to accelerate healing of the wound.

Accordingly, in accordance with the invention, the beneficial effects of absorbing exudates from the wound in a hydrophile layer are combined with this electric treatment, without sacrificing in any way the absorption capacity of the hydrophile layer used which, in the prior art, had to be rendered initially conductive by a charge of water and mineral salts, to the detriment of its total capacity to absorb exudates.

In this regard, the FIG. 8 graph shows that after about 7 hours (420 minutes) the hydrophile layer 8 was charged with approximately 1000 g/m$^2$ of exudates to reach a conductivity compatible with electric treatment of the wound, such charging being advantageously substituted for the charging with saline solution used in the prior art to impart this conductivity to it.

In the present invention, the electric treatment is delayed for a few hours, which is of no account compared to the time for a wound to heal, which is ordinarily in the order of several days to several weeks. Furthermore, the absorption of the exudates by the hydrophile layer begins as soon as the dressing is applied, before electric treatment of the wound.

The layer 8 of the dressing in accordance with the present invention can be made from many dry hydrophile products, alone or in combination, for example in the form of fibres, dispersed particles or foam. The thickness of the layer is advantageously from 200 to 2000 μm, preferably from 300 to 1000 μm. If the layer is not inherently self-adhesive, the dressing can be provided with adhesive means for fixing the dressing to the skin of the patient, as mentioned above.

The dry hydrophile layer can be made from any material or dry hydrophile absorbing substances used in the manufacture of dressings for treating exuding wounds.

Thus it can be in the form of absorbent foams, in particular hydrophile polyurethane foams as used in so-called hydrocellular dressings, in the form of fibres based on absorbent materials, for example alginate fibres, such as sodium or calcium alginate fibres, or cellulose derivative fibres, in the form of non-woven compresses, in the form of freeze-dried gels and in the form of hydrocolloidal substances such as gels or hydrocolloidal masses such as those used in so-called hydrocolloid dressings.

In the context of the present invention, hydrocolloid masses are preferred for the dry hydrophile layer.

These hydrocolloid masses are formed principally of an adhesive elastomer chosen from polymers such as poly-isobutenes or sequenced poly(styrene-olefin-styrene) copolymers such as, for example, poly(styrene-isoprene-styrene) or poly(styrene-ethylene butylene-styrene), associated or not with so-called sticky "tackifying" resins, plasticisers, etc and one or more hydrocolloids. The hydrocolloids usable in the masses referred to here are substances routinely used by the skilled person, known for their ability to absorb hydrophile liquids, in particular water and exudates, and to transport them rapidly. Appropriate hydrocolloids include, for example, polyvinyl alcohol, gelatine, pectin, natural vegetable gums such as carob gum, Karaya gum, guar gum, gum arabic, etc, cellulose derivatives such as hydroxyethylcelluloses, hydroxypropylcelluloses, carboxymethylcelluloses and their alkaline metal salts, such as their sodium or calcium salts. These hydrocolloids can be used alone or in combination.

Such masses are described in patent applications EP-A-130 061, EP-092 999 and WO-98/10801 and in U.S. Pat. No. 3,972,328.

The flexible support 1 can be cut out from a film of plastics material such as polyethylene, polyurethane, polyester or a polyimide. The electrodes 2 and 3 can be formed by screen printing a conductive ink onto this film. An Ag/AgCl type ink can be used to form so-called "sacrificial" electrodes adapted to prevent electrolysis of the water and therefore to maintain the pH of the exudates in the layer 8 of the wound constant, if required.

The electrodes 2, 3 can also be of metal, for example copper, zinc, silver or platinum, or of carbon or a conductive polymer.

The strip 4 is made from a material adapted to constitute a barrier to electricity and to moisture, such as a plastics material foam.

The "return" electrode 2 is covered with a layer 7 of a material assuring good contact with the skin and return flow of the current. This layer can be of polyoxyethylene or polyethylene-glycol, for example, cross-linked and containing sufficient water and salts to be a good conductor of electricity.

The structure of one embodiment of the electric supply means of the device in accordance with the invention will now be described with reference to FIG. 7. When these means are integrated into the dressing, as mentioned above, they take the form of an electronic circuit whose components (battery, discrete or integrated components) are mounted on conductive tracks formed on the support 1 by any technique known in the art: refusion, adhesive bonding, wave soldering, etc. They can also be removable and re-usable, or even entirely separate from the dressing, to which they are then connected by appropriate electrical connections.

In the embodiment of this circuit shown diagrammatically in FIG. 7, the circuit essentially includes one or more electric batteries 10, for example of the "button" cell type, adapted to provide an autonomous electric supply of the circuit, of low weight and with overall dimensions compatible with the portable nature of the dressing on which it is mounted, at least in the case of the embodiment of the dressing shown in FIG. 3. The battery 10 feeds a switch-mode power supply 12 which increases the voltage at the terminals of the battery to supply a current generator 13 of any suitable type, for example the Howlland type. This generator feeds current into the electrodes 2, 3 under the control of a sub-circuit 14.

According to the present invention, when the treatment begins the dry hydrophile layer 8 has substantially infinite impedance because it has not been hydrated by exudates from the wound. For a suitable electric current to flow, for example a current in the order of 1 mA, it is necessary to wait until hydration of the layer has reduced its impedance to a sufficiently low value, for example in the order of a few k$\Omega$.

Thus at the beginning of the treatment, the sub-circuit 14 initially controls a generator 13 in such a way that it passes, or attempts to pass, a low current between the electrodes, sufficient only to enable measurement of the impedance of the layer 8 by the sub-circuit 15. This circuit compares the measured impedance to a predetermined threshold, enabling detection of the sudden drop in impedance shown in the FIG. 9 graph. When that threshold is reached, after 6 to 8 hours, for example, the sub-circuit 14 switches the output current of the generator 13 to a predetermined nominal current, corresponding to saturation of the generator, for example. The electric treatment of the wound can then begin.

It can develop in time in accordance with a predetermined program, alternating time intervals $\Delta T_{ON}$ in which current flows in the wound and time intervals $\Delta T_{OFF}$ in which no current flows in the wound. The succession of time intervals can be programmed and controlled by a microcontroller 16 and by time counters 17, 18 incorporated in the microcontroller, as shown here, or external thereto.

It is now clear that the invention achieves the stated objects, namely to provide a device for treating a wound by electrotherapy including a layer for absorbing exudates from the wound whose capacity to absorb the exudates is not compromised by the necessity to render the layer electrically conductive. Note that, in the embodiment of the device shown in FIG. 3, the device has a particularly compact form, similar to that of a conventional dressing, the electrotherapy treatment means being integrated into the dressing.

Of course, the invention is not limited to the embodiments shown in FIGS. 1 to 3. Thus the electrodes of the device, which are adjacent in the embodiment of FIGS. 1 to 3, could also be concentric, as shown in FIG. 4, in which reference numbers identical to the reference numbers used in FIG. 1 represent identical or similar elements or units. The dry hydrophile layer 8 is then placed at the centre and the conductive layer 7 placed on the return electrode 2 has a closed contour, this layer being separated from the layer 8 by an insulative strip 4, which also has a closed contour.

The dressing can include only the active electrode (3), as in the embodiment of the device in accordance with the invention shown in FIG. 5. In this case, the return electrode (2) is formed of a support (1') separate from a support (1) of the active electrode (2) of the dressing and is totally independent of the dressing. For the electric supply of the dressing it is then necessary to provide the means shown in FIG. 6 including a circuit 9 of the type described in relation to the description of the embodiment of FIGS. 1 to 3 and flexible electric lines such as the lines 20, 21, 22 for connecting the poles 23, 24 of the circuit to the contact studs 5, 6 of the electrodes of the FIG. 5 embodiment, via clamps 25, 26, 27, 28, 29. Note that the clamps 28, 29 are used to connect two return electrodes to the circuit 9. The number of return electrodes, installed at a distance from the electrode which is applied to the wound to be treated, can obviously be varied to obtain a more regular distribution of the therapeutic current in the wound.

What is claimed is:

1. A device for therapeutic treatment of wounds, said device comprising:
    a dressing for contact with a wound and provided with a dry hydrophilic layer for absorbing exudates from the wound, said layer, upon said contact, being free of sufficient hydrating material for electrical conductivity; and
    electric supply means for circulating a current in said wound through said dressing, activation of said electric supply means being controlled by subsequent migration of exudates into said layer concomitantly with continuation of a process of exudate absorption by said layer.

2. The device according to claim 1, wherein said dry hydrophilic layer is chosen from the group consisting of polyurethane foams, non-woven compresses, hydrocolloid masses and gels, fibres of alginates and cellulose derivatives in the form of freeze-dried gels.

3. The device according to claim 1, wherein said dressing includes two electrodes formed on a common plane support, one of said electrodes being covered with said dry hydrophilic layer, said supply means being connected to said electrodes to cause an electric current to flow between them.

4. The device according to claim 3, wherein said electrodes are adjacent.

5. The device according to claim 3, wherein said electrodes are concentric.

6. The device according to claim 1, wherein said dressing includes an active electrode formed on a plane support, said active electrode being covered with said dry hydrophilic layer, and said device includes at least one return electrode formed on a plane support separate from that of said active electrode, said supply means being connected to said active and return electrodes to cause an electric current to flow between them.

7. The device according to claim 1, wherein said dressing includes adhesive means enabling said dressing to be fixed to the skin of a patient.

8. The device according to claim 1, wherein said electric supply means include means for controlling the output current.

9. The device according to claim 8, wherein said electric supply means include means for controlling the output current in time.

10. The device according to claim 8, wherein said supply means include a circuit for measuring the impedance of the hydrophilic layer and means responsive to said measurement falling below a predetermined threshold to activate the supply means under nominal conditions.

11. The device according to claim 1, wherein said supply means are integrated into the dressing.

12. The device according to claim 1, wherein said device includes means for removably mounting said supply means on the dressing.

13. The device according to claim 1, wherein said dry hydrophilic layer is free of all hydrating material upon contact with a wound.

14. A dressing for use in a device for therapeutic treatment of wounds and for contacting a wound when in use, said dressing comprising:

a dry hydrophilic layer for absorbing exudates from a wound, said layer being free of sufficient hydrating material for electrical conductivity when initially put into use; and an electrode formed on a planar support and covered with said dry hydrophilic layer.

15. The dressing according to claim 14, wherein said dry hydrophilic layer is free of all hydrating material when initially put into use.

16. The dressing according to claim 14, wherein said layer is charged through absorption of wound exudates and as a result becomes electrically conductive following a period of use.

17. The dressing according to claim 14, wherein said dry hydrophilic layer is a hydrocolloid mass.

18. A device for therapeutic treatment of wounds, said device comprising:

a dressing for absorbing exudates from a wound when in use, said dressing including a dry hydrophilic layer which, when initially put into use, is free of sufficient hydrating material to effect electrical conductivity in said layer; and electronic circuitry for circulating a current in said wound through said dressing, activation of said electronic circuitry being dependent upon exudate absorption by said layer.

19. The device according to claim 18, wherein said dry hydrophilic layer is free of all hydrating material when initially put into use.

20. The device according to claim 18, wherein said layer becomes electrically conductive as a result of exudate absorption over a period of use.

* * * * *